(12) United States Patent
Hsieh et al.

(10) Patent No.: US 7,394,887 B2
(45) Date of Patent: Jul. 1, 2008

(54) METHOD AND APPARATUS FOR RECONSTRUCTION OF TILTED CONE BEAM DATA

(75) Inventors: Jiang Hsieh, Brookfield, WI (US); Xiangyang Tang, Waukesha, WI (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 10/966,415

(22) Filed: Oct. 15, 2004

(65) Prior Publication Data
US 2006/0083345 A1   Apr. 20, 2006

(51) Int. Cl.
*A61B 6/03* (2006.01)
(52) U.S. Cl. ............................................ 378/17; 378/20
(58) Field of Classification Search .................... 378/17, 378/4, 20
See application file for complete search history.

(56) References Cited

U.S. PATENT DOCUMENTS

| | | | |
|---|---|---|---|
| 4,411,012 A * | 10/1983 | Pfeiler et al. | 378/17 |
| 5,046,003 A * | 9/1991 | Crawford | 378/15 |
| 5,257,183 A | 10/1993 | Tam | |
| 5,365,560 A | 11/1994 | Tam | |
| 5,390,226 A | 2/1995 | Tam | |
| 5,461,650 A | 10/1995 | Tam | |
| 5,663,995 A * | 9/1997 | Hu | 378/15 |
| 5,671,265 A | 9/1997 | Andress | |
| 5,802,133 A | 9/1998 | Kawai et al. | |
| 5,909,476 A | 6/1999 | Cheng et al. | |
| 6,075,836 A | 6/2000 | Ning | |
| 6,229,869 B1 | 5/2001 | Hu | |
| 6,324,241 B1 | 11/2001 | Besson | |
| 6,324,246 B1 * | 11/2001 | Ruimi | 378/15 |
| 6,463,117 B1 | 10/2002 | Hsieh | |
| 6,490,333 B1 | 12/2002 | Hsieh | |
| 6,678,346 B2 | 1/2004 | Hsieh | |
| 6,751,283 B2 * | 6/2004 | van de Haar | 378/17 |
| 6,775,347 B2 | 8/2004 | Hsieh et al. | |
| 2004/0028173 A1 | 2/2004 | van de Haar | |

FOREIGN PATENT DOCUMENTS

WO     WO99/01066     1/1999

OTHER PUBLICATIONS

Ilmar Hein et al., "Feldkamp-based cone-beam reconstruction for gantry-tilted helical multislice CT", Medical Physics, Dec. 2003, pp. 3233-3242, vol. 30, No. 12, University of Massachusetts Medical School, Worcester, Massachusetts, USA.

(Continued)

*Primary Examiner*—Chih-Cheng Glen Kao
(74) *Attorney, Agent, or Firm*—The Small Patent Law Group; Dean D. Small (57) ABSTRACT

A method for reconstructing tilted cone beam data acquired using a CT apparatus. The CT apparatus has a gantry and a table. The gantry has an x-ray source and a detector array with columns and rows. The gantry is tilted at a gantry tilt angle with respect to the table and a plurality of projection data is acquired using the CT apparatus. Fan-parallel rebinning is performed on a row by row basis to form a plurality of reconstructed pixels. The coordinate locations of the plurality of reconstructed pixels are adjusted based on the gantry tilt angle and used to form a reconstructed image.

16 Claims, 4 Drawing Sheets

OTHER PUBLICATIONS

Jiang Hsieh et al., "Tomographic Reconstruction for Tilted Helical Multislice CT", IEEE Transactions on Medical Imaging, Sep. 2000, pp. 864-872, vol. 19, No. 9, University of Massachusetts Medical School, Worcester, Massachusetts, USA.

Bruce D. Smith, "Image Reconstruction from Cone-Beam Projections: Necessary and Sufficient Conditions and Reconstruction Methods", IEEE Transactions on Medical Imaging, Mar. 1985, pp. 14-25, vol. MI-4, No. 1, published by IEEE, USA.

Pierre Grangeat, "Mathematical Framework of Cone Beam 3D Reconstruction via the First Derivative of the Radon Transform", Mathematical Methods in Tomography, Lecture Notes in Mathematics, 1991, pp. 66-97, Springer-Verlag, New York, USA.

L.A. Feldkamp et al., 'Practical cone-beam algorithm, Journal of the Optical Society of America, Jun. 1984, vol. 1, No. 6, pp. 612-619, Optical Society of America, USA.

Y. Weng et al., "A Reconstruction Algorithm for Helical Cone-Beam SPECT", IEEE Transactions On Nuclear Science, Aug. 1993, vol. 40, No. 4, IEEE, USA.

Bruce D. Smith, "Cone-beam tomography: recent advanced and a tutorial review", Optical Engineering, May 1990, pp. 524-534, vol. 29, No. 5, SPIE—The International Society for Optical Engineering, USA.

Heang K. Tuy, An Inversion Formula for Cone-Beam Reconstruction, SIAM Journal on Applied Mathematics, Jun. 1983, vol. 43, No. 3, Society for Industrial and Applied Mathematics, USA.

* cited by examiner

METHOD AND APPARATUS FOR RECONSTRUCTION OF TILTED CONE BEAM DATA

BACKGROUND OF THE INVENTION

This invention relates generally to computed tomography (CT) imaging apparatus; and more particularly, to the processing of scan data collected when the CT gantry is tilted.

In at least one known computed tomography (CT) imaging system configuration, an x-ray source projects a fan-shaped beam which is collimated to lie within an X-Y plane of a Cartesian coordinate system and generally referred to as the "imaging plane". The x-ray beam passes through the object being imaged, such as a patient. The beam, after being attenuated by the object, impinges upon an array of radiation detectors. The intensity of the attenuated beam radiation received at the detector array is dependent upon the attenuation of the x-ray beam by the object. Each detector element of the array produces a separate electrical signal that is a measurement of the beam attenuation at the detector location. The attenuation measurements from all the detectors are acquired separately to produce a transmission profile.

In known third generation CT systems, the x-ray source and the detector array are rotated with a gantry within the imaging plane and around the object to be imaged so that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles, or view angles, during one revolution of the x-ray source and detector. In an axial scan, the projection data is processed to construct an image that corresponds to a two dimensional slice taken through the object. One method for reconstructing an image from a set of projection data is referred to in the art as the filtered back projection technique. This process converts the attenuation measurements from the scan into integers called "CT numbers" or "Hounsfield units", which are used to control the brightness of a corresponding pixel on a cathode ray tube display.

Cone beam scanning is performed using a multi-dimensional detector array instead of a linear detector array as is used in a fan beam scan. In a cone beam helical scan, the x-ray source and the multi-dimensional detector array are rotated with a gantry within the imaging plane as the patient is moved in the z-axis synchronously with the rotation of the gantry. Such a system generates a multi-dimensional helix of projection data. In a cone beam step-and-shoot scan, the table is held stationary while the x-ray source and multi-dimensional detector array are rotated about the z-axis and a slice of data is acquired. The table is then moved to a next position along the z-axis to acquire the next scan slice. This process is repeated until the desired portion of the patient has been scanned.

In many clinical applications, the CT gantry is tilted to avoid direct exposure of the patient retina to the x-ray radiation or to ensure optimal spatial resolution. In the past, several algorithms have been proposed to correct the artifacts caused by the geometric change in the gantry tilt. These algorithms deal only with multi-slice configurations in the fan beam or cone beam reconstruction process. That is, the projection samples are filtered and backprojected in the same geometry as the data acquisition. Consequently, all the samples from a single view have a common intersection point which corresponds to the x-ray source location. It has been shown that such reconstruction process produces inferior noise characteristics due to the scaling factor in the backprojection step (the scaling factor is proportional to the inverse of the distance squared from the reconstructed pixel to the x-ray source).

Thus, a system and method are desired to improve the image noise homogeneity when the CT gantry is tilted that addresses the problems notes above and others previously experienced.

BRIEF DESCRIPTION OF THE INVENTION

In one embodiment, a method for reconstructing tilted cone beam data acquired using a CT apparatus. The CT apparatus has a gantry and a table. The gantry has an x-ray source and a detector array with columns and rows. The gantry is tilted at a gantry tilt angle with respect to the table and a plurality of projection data is acquired using the CT apparatus. Fan-parallel rebinning is performed on a row by row basis to form a plurality of reconstructed pixels. The coordinate locations of the plurality of reconstructed pixels are adjusted based on the gantry tilt angle and used to form a reconstructed image.

In another embodiment, a method for reconstructing tilted cone beam data acquired using a CT apparatus having a gantry and a table. The gantry has an x-ray source and a detector array with columns and rows. The gantry is tilted at a gantry tilt angle with respect to the table and a plurality of projection data is acquired using the CT apparatus. The projection data is fan-parallel rebinned to form a plurality of parallel views comprising a plurality of reconstructed pixels. A table travel distance is calculated for each parallel view. Coordinate locations of the plurality of reconstructed pixels are adjusted based on the table travel distance corresponding to each parallel view. The plurality of reconstructed pixels are utilized to form a reconstructed image.

In another embodiment, an apparatus for acquiring computed tomography data and reconstructing an image of an object. The apparatus has a gantry, a table with a table motor controller for moving the table, a data acquisition system, and a computer. The table holds an object of interest and the gantry is tilted at a gantry tilt angle with respect to the table. The gantry has an x-ray source projecting a cone beam of x-rays through an object of interest and a detector array with a plurality of detector elements arranged in rows and columns. The detector elements detect a projected image of the x-rays passing through the object of interest. The projected image comprises a plurality of projection data. The data acquisition system receives the projection data from the detector array. The computer processes fan-parallel rebins the projection data on a row by row basis to form a plurality of reconstructed pixels. The computer adjusts the coordinate locations of the plurality of reconstructed pixels based on the gantry tilt angle, and the reconstructed pixels are used to form a reconstructed image.

DETAILED DESCRIPTION OF THE INVENTION

Figure 1:
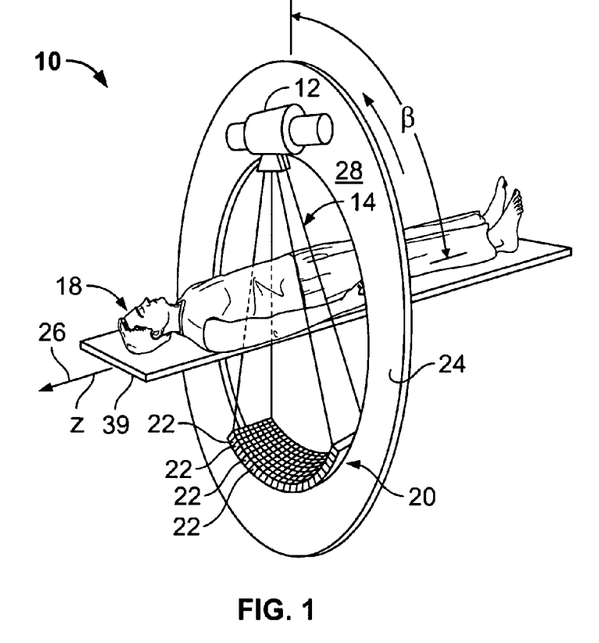
FIG. 1 is a pictorial view of a CT imaging system formed in accordance with an embodiment of the present invention.

FIG. 1 illustrates a CT imaging system 10 formed in accordance with an embodiment of the present invention. The CT imaging system 10 includes an x-ray source 12 oriented to project a cone beam 14 of x-rays from a focal spot 16 (FIG. 2) through a patient 18 to be received by a two-dimensional detector array 20. The two-dimensional detector array 20 includes a number of detector elements 22 arranged over the area of the detector array 20 in generally perpendicular columns and rows to detect a projected image of the x-rays 14 passing through the patient 18. The rows of detector elements 22 may extend along an in-slice dimension. By way of example only, each row may include 1,000 separate detector elements 22, and the array 20 may include 16 rows disposed along the slice dimension. The detectors 22 may be gas or solid state detectors which produce an electrical signal proportional to the x-ray flux received over the sample period.

The x-ray source 12 and the two-dimensional detector array 20 are mounted on either side of a gantry 24 so as to rotate about an axis of rotation, or z-axis 26, generally positioned within the patient 18. The axis of rotation forms the z-axis 26 of a Cartesian coordinate system having its origin centered within the cone beam 14. The plane defined by the x and y axes of this coordinate system thus defines a plane of rotation, specifically the gantry plane 28 of the gantry 24. Rotation of the gantry 24 is measured by angle β from an arbitrary reference position within the gantry plane 28. In helical acquisition, β typically varies over several rotations. β is also referred to herein as projection angle β.

Figure 2:
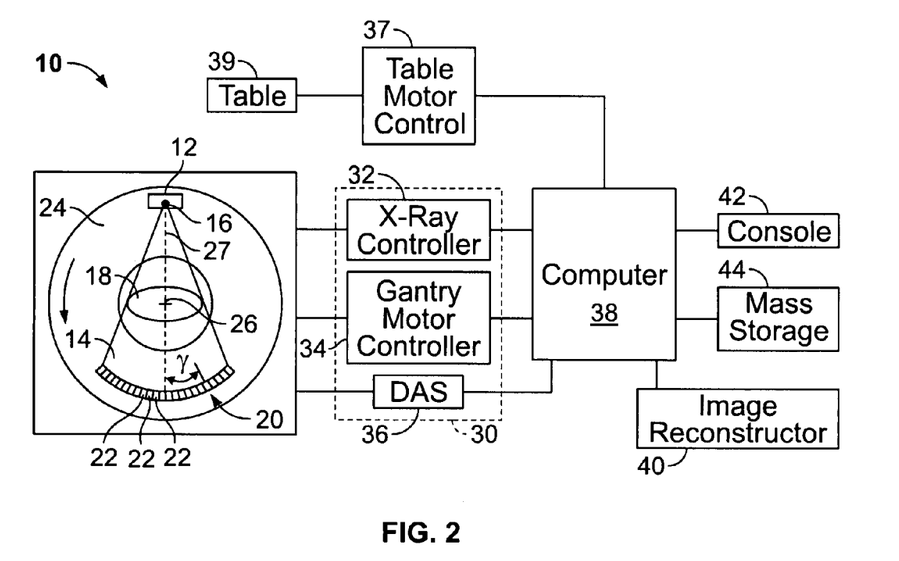
FIG. 2 is a block schematic diagram of the system illustrated in FIG. 1 formed in accordance with an embodiment of the present invention.

FIG. 2 illustrates a block diagram of the CT imaging system 10 formed in accordance with an embodiment of the present invention. The control subsystem of the CT imaging system 10 has gantry associated control modules 30 which include: x-ray controller 32, which provides power and timing signals to the x-ray source 12, and gantry motor controller 34, which controls the rotational speed and position of the gantry 24. A data acquisition system (DAS) 36 receives projection data from the two-dimensional detector array 20 and converts the data into digital form for later computer processing. The x-ray controller 32, the gantry motor controller 34 and the data acquisition system 36 are connected to computer 38. The computer 38 also governs operation of a table motor control 37 which drives a motor that moves the patient table 39 along the z-axis 26.

The computer 38 is a general purpose minicomputer programmed to acquire and manipulate projection data as will be described in detail below. The computer 38 is connected to an image reconstructor 40 which performs high speed image reconstruction according to methods known in the art.

The computer 38 receives commands and scanning parameters via operator console 42 which is generally a CRT display and keyboard that enables an operator to enter parameters for the CT scan and to display the reconstructed image. A mass storage device 44 provides a means for storing operating programs.

During data acquisition, the CT imaging system 10 functions as a conventional cone-beam system in gathering data. In the step-and-shoot acquisition method, the table 39 is held stationary as the x-ray source 12 and detector array 20 make a complete revolution around the gantry 24 about the z-axis 26. At each of a plurality of angular positions β, the attenuation data from all the detectors 22 in array 20 are stored in the mass memory 44. Upon completion of a full rotation, the computer 38 commands the table motor control 37 to advance the table 39 to another position along the z-axis 26 and another rotational scan of the patient 18 is performed. This process is repeated until the desired portion of the patient 18 has been fully scanned. Alternatively, the CT imaging system 10 may acquire data in the helical acquisition mode, wherein the table motor control 37 advances the table 39 as the x-ray source 12 and detector array 20 are rotated and scan data is acquired.

Figure 3:
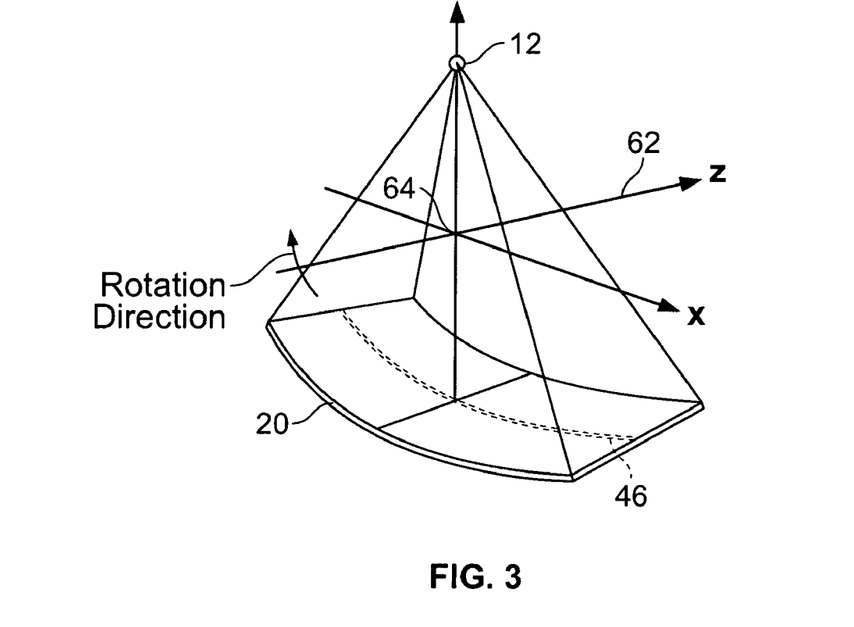
FIG. 3 illustrates an iso-center for a detector row in accordance with an embodiment of the present invention.

FIG. 3 illustrates an iso-center 64 for a detector row 46 in accordance with an embodiment of the present invention. In this example, the gantry 12 is not tilted with respect to a system z-axis 62. As discussed previously, detector array 20 has multiple detector rows 46. The iso-center 64 for detector row 46 falls on the z-axis 62, and the iso-centers for all rows within detector array 20 fall on the z-axis 62. For each row, the corresponding iso-center is the intersection of the z-axis 62 with the plane formed by the detector row and the x-ray source 12.

Figure 4:
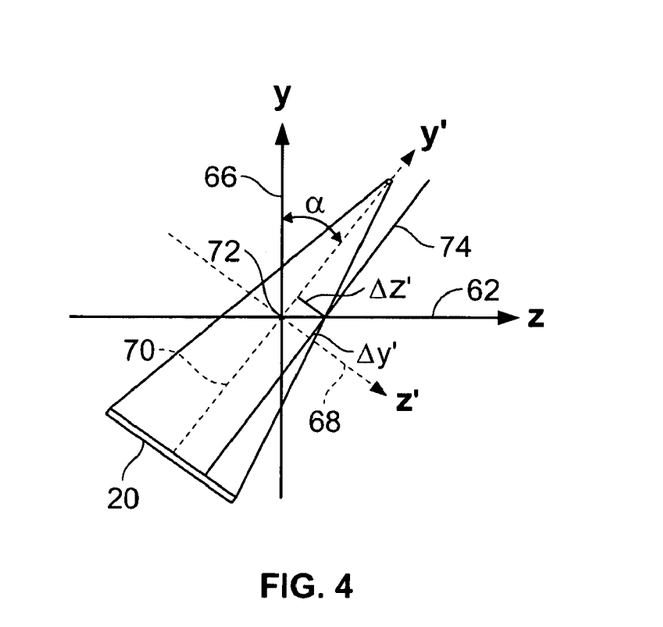
FIG. 4 illustrates a tilted geometry of the CT imaging system wherein the gantry, and thus the detector array, is tilted with respect to a system z-axis in accordance with an embodiment of the present invention.

FIG. 4 illustrates a tilted geometry of the CT imaging system 10 wherein the gantry 12, and thus the detector array 20, is tilted with respect to a system z-axis 62 in accordance with an embodiment of the present invention. Therefore, the detector array 20 has a detector rotation axis, z'-axis 68, which is different than the system z-axis 62. The detector array 20 has a detector center plane 70 which is perpendicular to the z'-axis 68, and passes through an iso-center 72 of the detector center plane 70. The iso-center 72 for each detector row 46 does not coincide with the iso-center 64 of the CT system 10 as illustrated in FIG. 3, but rather coincides with the z'-azis 68, system y-axis 66 and the detector center plane 70.

Image noise homogeneity of the processed scan data can be significantly improved by first performing fan or cone beam to parallel beam rebinning prior to performing back projection with an algorithm such as the Feldkamp algorithm. In such processing, the original fan beam or cone beam data is rebinned or re-interpolated into a set of parallel or tilted parallel beam samples. The reconstruction process is then applied to the parallel samples. The reconstruction algorithm associated with this process when the gantry 24 is tilted is presented below.

Figure 5:
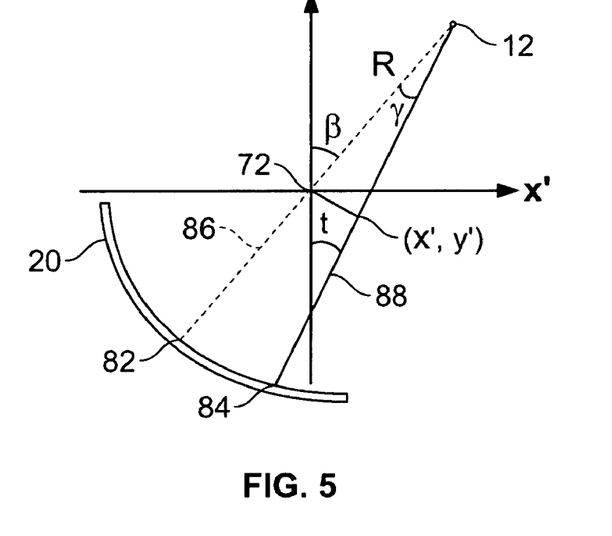
FIG. 5 illustrates the relationship between a fan beam sample, defined by (γ, β), and a parallel beam sample, defined by (t, β+γ), in accordance with an embodiment of the present invention.

FIG. 5 illustrates the relationship between a fan beam sample, defined by (γ, β), and a parallel beam sample, defined by (t, β+γ), in accordance with an embodiment of the present invention. An iso-ray 86 having the iso-center 72 and a ray 88 are illustrated. The angle formed between a detector cell 84 and a detector iso-cell 82 in the same detector row, and the x-ray source 12, is called γ. The angle formed by the iso-ray 86 and the y'axis is called β. In the fan beam sampling, ray 88 can be uniquely defined by (γ, β). In the parallel beam sampling, ray 88 can be uniquely defined by (t, β+γ), where t is the distance from the ray 88 to the iso-center 72. In other words, γ is the fan angle from which the original fan beam sample with the iso-ray is rebinned.

Figure 6:
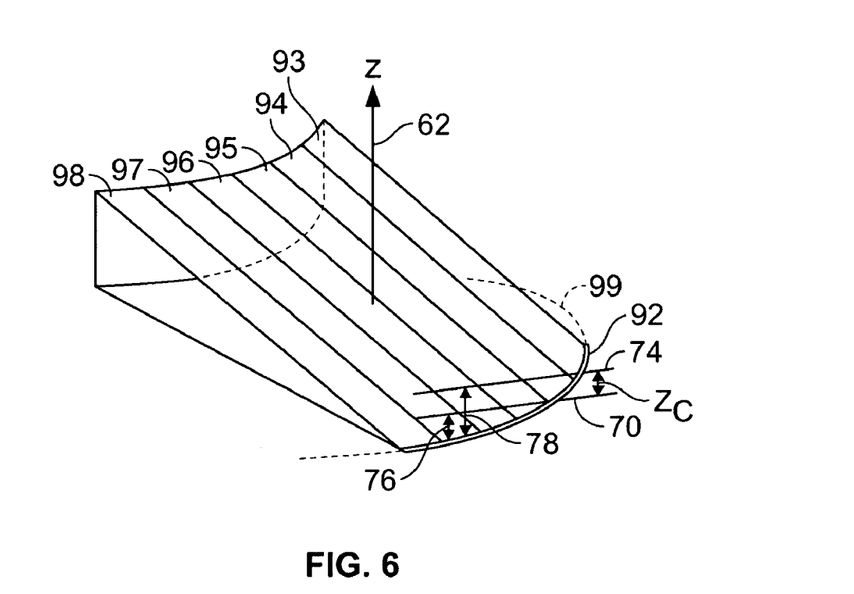
FIG. 6 illustrates fan-parallel rebinning in accordance with an embodiment of the present invention.

FIG. 6 illustrates fan-parallel rebinning in accordance with an embodiment of the present invention. Multiple x-ray source locations 92 fall onto a curve defined by a helical x-ray source trajectory 99. Parallel views 93–98 are formed by fan-parallel rebinning of multiple cone beam projections.

Additional complexities arise after the rebinning process as the source locations 92 are no longer a single point for each parallel view 93–98. Each source location 92 corresponds to a different z location on the system z-axis 62. The detector center plane 70 and a reconstruction plane 74 are also illustrated. When the reconstructed slice is the same as the detector center plane 70, a Δz shift 76 is estimated. When a reconstruction plane 74 differs from, but is parallel to, the detector center plane 70, a Δz shift 78 is estimated.

Returning to FIG. 5, for the tilted step-and-shoot acquisition mode, the iso-center 72 for each detector row 46 needs to be remapped on a slice-by-slice basis. In the tilted helical acquisition mode, the table 39 does not travel perpendicular to the detector center plane 70, or along the z'-axis 68. Instead, the table 39 travels along the z-axis 62. As a result, the adjustment of the iso-center 72 depends not only on the projection angle β, but also on the location of the reconstructed pixel. The tilted helical case will be discussed first followed by the step-and-shoot mode.

During the fan-parallel rebinning process, there is a fixed relationship between a parallel distance to the iso (t) and the projection angle (β+Δβ) that the fan beam sample 88 comes from. β is the projection angle of the parallel view to be rebinned, based on the iso-ray 86 and the ray 88 of the same parallel projection. This relationship is described by Equation 1.

$$\Delta\beta = -\gamma = -\sin^{-1}\left(\frac{t}{R}\right) \qquad \text{Equation 1}$$

wherein R is the distance between the x-ray source 12 and the iso-center 72, γ is the fan angle from which the original cone beam sample is rebinned, and t is the distance between the iso-center 72 and the fan beam sample 88. As stated previously and for ease of discussion, Equation 1 assumes that the detector center plane 70 coincides with the reconstruction plane 74 at a center view angle, $\beta_c$. Additionally, it should be understood that the fan-parallel rebinning and the pixel and image reconstruction processing may be accomplished by the computer 38 and/or image reconstructor 40.

In helical scan mode, the table 39 travels at a constant speed and the location of the x-ray source 12 scales proportionally with the projection angle β. In other words, the x-ray source 12 and the table 39 both move at constant speeds, and thus are linearly related. Therefore, the amount of angular change, Δβ, corresponds to a distance the table 39 travels along the z-axis, Δz, as described by Equation 2.

$$\Delta z = \frac{p \cdot W}{2\pi}\Delta\beta = \frac{p \cdot W}{2\pi}\sin^{-1}\left(\frac{t}{R}\right) \qquad \text{Equation 2}$$

wherein p is the helical pitch and W is the width of the x-ray beam at the iso-center 72.

The distance t from ray 88 passing through any reconstructed pixel (x', y') (which is any point along ray 88) to the iso-center 72 at the projection angle β can be calculated by using Equation 3:

$$t = x'\cos(\beta) + y'\sin(\beta) \qquad \text{Equation 3}$$

Distance t may now be replaced by (x', y') because in the image reconstruction, the amount of z shift for each reconstructed pixel (x', y') is desired. Therefore, Equations 2 and 3 may be combined to form Equation 4.

$$\Delta z = \frac{p \cdot W}{2\pi}\sin^{-1}\left(\frac{x'\cos(\beta) + y'\sin(\beta)}{R}\right) \qquad \text{Equation 4}$$

In helical acquisition mode, the table 39 does not travel perpendicular to the detector center plane 70, or along the z'-axis, but instead travels along the z-axis 62 of the CT imaging system 10. Therefore, the total amount of table traveling distance relative to the reconstruction plane 74 may be calculated using Equation 5. Alternatively, the Δz may be described as the change in the x-ray source 12 location.

$$\Delta z = \frac{p \cdot W}{2\pi}\sin^{-1}\left(\frac{x'\cos(\beta) + y'\sin(\beta)}{R}\right) + \frac{(\beta - \beta_c)p \cdot W}{2\pi} \qquad \text{Equation 5}$$

Equation 5

Next, the case where the reconstruction plane 74 is different from the detector center plane 70 will be discussed. Turning to FIG. 6, the reconstruction plane 74 is a distance $z_c$ from the detector center plane 70. Therefore, an adjustment in the z plane is calculated with Equation 6, which incorporates an additional adjustment by adding $z_c$ to Equation 5.

$$\Delta z = \frac{p \cdot W}{2\pi}\left[\beta - \beta_c + \sin^{-1}\left(\frac{x'\cos(\beta) + y'\sin(\beta)}{R}\right)\right] + z_c \qquad \text{Equation 6}$$

Equation 6

Thus, Equation 6 also replaces Equation 5 when the detector center plane 70 coincides with the reconstruction plane 74 because $z_c=0$.

Figure 7:
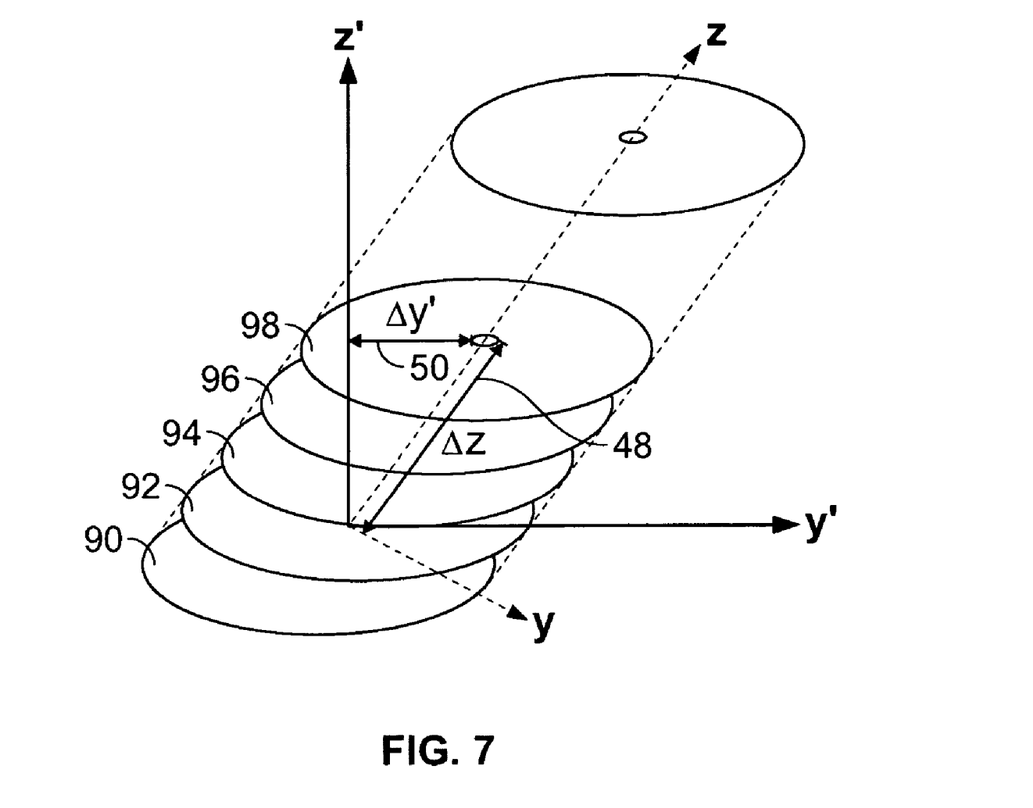
FIG. 7 illustrates the reconstruction plane coordinates in accordance with an embodiment of the present invention.

FIG. 7 illustrates the reconstruction plane coordinates in accordance with an embodiment of the present invention. Coordinate system (x-y-z) represents images acquired while the gantry 24 is not tilted, while coordinate system (x'-y'-z) represents images acquired while the gantry 24 is tilted with respect to the CT imaging system 10 z-axis 26. In the tilted helical reconstruction, reconstructed images are a stack of slices 90–98 which are parallel to the (x'-y') plane and centered on the z-axis. Consequently, the coordinate system of the stack of slices 90–98 is (x'-y'-z). Therefore, the amount of adjustment in y' is calculated in Equation 7. In other words, a shift 48, or adjustment Δz, corresponds to an iso-shift 50, or adjustment Δy', in the corresponding slices 90–98.

$$\Delta y' = \Delta z \cdot \sin(\alpha) \qquad \text{Equation 7}$$

Equations 6 and 7 dictate the amount of coordinate adjustment that needs to be performed during the back projection process. For reconstruction, the reconstructed image is in the x'-y'-z coordinate system. Therefore, the coordinate adjustment is shown in Equation 8, and each reconstructed pixel at location (x', y', z) is mapped into a new coordinate system (x", y", z").

$$\begin{cases} x'' = x', \\ y'' = y' + \Delta y', \\ z'' = z + \Delta z. \end{cases} \qquad \text{Equation 8}$$

When acquiring data in the tilted step-and-shoot scanning mode, the helical pitch p=0. Therefore, the step-and-shoot mode of operation is a special case of the tilted helical mode of operation in which the helical pitch equals zero and the reconstructed pixel is not adjusted in the y' plane. By substituting p=0 into all equations, Equation 9 now defines the mapping for the tilted step-and-shoot scanning mode:

$$\begin{cases} x'' = x', \\ y'' = y' + z_c \cdot \sin(\alpha), \\ z'' = z + z_c. \end{cases} \quad \text{Equation 9}$$

Back projection can now be preformed on the new coordinates according to known back projection methods.

While the invention has been described in terms of various specific embodiments, those skilled in the art will recognize that the invention can be practiced with modification within the spirit and scope of the claims.

What is claimed is:

1. A method for reconstructing tilted cone beam data acquired using a computed tomography (CT) apparatus having a gantry and a table, said gantry comprising an x-ray source and a detector array having columns and rows, said method comprising:
    acquiring a plurality of projection data using the CT apparatus wherein said gantry is tilted at a gantry tilt angle with respect to said table, wherein said projection data comprises a first coordinate system having a z'-axis corresponding to said gantry tilt angle and said CT apparatus comprises a second coordinate system having a z-axis corresponding to a movement of said table, said z'-axis and said z-axis being different, and further moving said table along said z-axis while acquiring said projection data;
    calculating a distance said table travels along said z-axis, said distance comprising components in two different directions relative to said first coordinate system;
    fan-parallel rebinning said projection data to form a plurality of reconstructed pixels, said fan-parallel rebinning being performed on a row by row basis;
    adjusting coordinate locations of said plurality of reconstructed pixels based on said gantry tilt angle and said distance to form an adjusted plurality of reconstructed pixels; and
    forming a reconstructed image based at least on the adjusted plurality of reconstructed pixels.

2. The method of claim 1, further comprising:
    said projection data comprising a first coordinate system corresponding to said gantry tilt angle; and
    said CT apparatus comprising a second coordinate system corresponding to a movement of said table, said first and second coordinate systems being different.

3. The method of claim 1, further comprising:
    said projection data comprising a first coordinate system corresponding to said gantry tilt angle;
    said CT apparatus comprising a second coordinate system corresponding to a movement of said table, said first and second coordinate systems being different; and
    the fan-parallel rebinning step further comprising forming a plurality of parallel views comprising said plurality of reconstructed pixels, said plurality of reconstructed pixels having a set of first coordinates in said first coordinate system.

4. The method of claim 1, further comprising:
    said projection data comprising a first coordinate system corresponding to said gantry tilt angle;
    said CT apparatus comprising a second coordinate system corresponding to a movement of said table, said first and second coordinate systems being different;
    the fan-parallel rebinning step further comprising forming a plurality of parallel views comprising said plurality of reconstructed pixels, said plurality of reconstructed pixels having a set of first coordinates in said first coordinate system; and
    mapping said plurality of reconstructed pixels into said second coordinate system based on said adjusting step, said reconstructed image being based on said second coordinate system.

5. The method of claim 1, further comprising:
    said projection data comprising a first coordinate system corresponding to said gantry tilt angle;
    said CT apparatus comprising a second coordinate system corresponding to a movement of said table, said first and second coordinate systems being different;
    the fan-parallel rebinning step further comprising forming a plurality of parallel views comprising said plurality of reconstructed pixels, said plurality of reconstructed pixels having a set of first coordinates in said first coordinate system;
    mapping said plurality of reconstructed pixels into said second coordinate system based on the adjusting step; and
    performing back projection on each of said plurality of reconstructed pixels to form said reconstructed image, said reconstructed image being based in said second coordinate system.

6. The method of claim 1, the adjusting step further comprising calculating an adjustment based on at least one of a projection angle and a helical pitch, said adjustment shifting said coordinate locations of said plurality of reconstructed pixels.

7. The method of claim 1, the adjusting step further comprising adjusting coordinate locations of said plurality of reconstructed pixels on a pixel by pixel basis.

8. A method for reconstructing tilted cone beam data acquired using a computed tomography (CT) apparatus having a gantry and a table, said gantry comprising an x-ray source and a detector array having columns and rows, said method comprising:
    acquiring a plurality of projection data at a plurality of projection angles using said CT apparatus wherein said gantry is tilted at a gantry tilt angle with respect to said table; said projection data having a first coordinate system comprising a first axis corresponding to said gantry tilt angle, said first coordinate system having an iso-center corresponding to each of said projection angles, the CT apparatus having a second coordinate system comprising a second axis corresponding to a movement of said table;
    fan-parallel rebinning said projection data to form a plurality of parallel views comprising a plurality of reconstructed pixels;
    calculating a distance from a reconstructed pixel to said iso-center at a corresponding projection angle, said distance used to calculate a shift moving said reconstructed pixel along said first axis;
    calculating a table travel distance for each parallel view, said table travel distance being based on at least said distance from a reconstructed pixel to said iso-center;

adjusting coordinate locations of said plurality of reconstructed pixels based on said table travel distance corresponding to each said parallel view to form an adjusted plurality of reconstructed pixels; and forming a reconstructed image based at least on the adjusted plurality of reconstructed pixels.

9. The method of claim 8, wherein said first and second coordinate systems are different.

10. The method of claim 8, further comprising:
said detector array further comprising a detector center plane; and
calculating a distance from said detector center plane to a reconstruction plane, said table travel distance being calculated relative to said reconstruction plane, said reconstructed image being within said reconstruction plane.

11. The method of claim 8,
the step of calculating said table travel distance further comprising calculating said table travel distance based on at least one of a helical pitch of said CT apparatus and a width of an x-ray beam at said iso-center.

12. The method of claim 8,
said CT apparatus further comprising having a helical pitch equal to zero, said table travel distance being calculated with respect to said helical pitch.

13. An apparatus for acquiring computed tomography data and reconstructing an image of an object, said apparatus comprising:
a gantry comprising an x-ray source projecting a cone beam of x-rays through an object of interest, said gantry further comprising a detector array having a plurality of detector elements arranged in rows and columns, said detector elements detecting a projected image of said x-rays passing through the object of interest, said projected image comprising a plurality of projection data;
a table for holding said object of interest, said gantry being tilted at a gantry tilt angle with respect to said table;
a table motor controller for moving said table;
a data acquisition system configured to receive said projection data from said detector array including acquiring a first set of projection data while said table is stationary at a first location, wherein said table motor controller moves said table to a second location prior to acquiring a second set of projection data, the first and second sets of projection data acquired at a plurality of projection angles, said first and second sets of projection data having a first coordinate system comprising a first axis corresponding to said gantry tilt angle, said first coordinate system having an iso-center corresponding to each of said projection angles, the gantry and table having a second coordinate system comprising a second axis corresponding to a movement of said table; and a computer configured to process said projection data, said computer fan-parallel rebinning said projection data to form a plurality of reconstructed pixels, said fan-parallel rebinning being performed on a row by row basis, said computer calculating a distance from a reconstructed pixel to said iso-center at a corresponding projection angle, said distance used to calculate a shift moving said reconstructed pixel along said first axis, said computer adjusting coordinate locations of said plurality of reconstructed pixels based on said gantry tilt angle and a table travel distance to form an adjusted plurality of reconstructed pixels, the table travel distance corresponding to each of a plurality of parallel views and based on at least said distance from a reconstructed pixel to said iso-center, the adjusted plurality of reconstructed pixels being utilized to form a reconstructed image.

14. The apparatus of claim 13, said data acquisition system further configured to acquire said projection data while said table motor controller moves said table, said projection data further comprising a multi-dimensional helix of projection data.

15. The apparatus of claim 13, further comprising:
said cone beam of x-rays further comprising having a width at said iso-center; and
said computer further configured to adjust said coordinate locations of said plurality of reconstructed pixels based on at least said width.

16. The apparatus of claim 13, further comprising
a gantry motor controller rotating said x-ray source and said detector array while said table motor controller moves said table;
an x-ray controller directing said x-ray source to project said cone beam of x-rays at a plurality of projection angles while said x-ray source and said detector array are rotating;
said data acquisition system further configured to acquire said projection data while said table motor controller moves said table, said projection data further comprising a multi-dimensional helix of projection data; and
said computer configured to adjust said iso-center based on said projection angles and said coordinate locations of said reconstructed pixels.

* * * * *